United States Patent
Lowry

(10) Patent No.: US 9,474,572 B2
(45) Date of Patent: Oct. 25, 2016

(54) COMPRESSION SPRING AUTOMATED RETRACTABLE PROTECTIVE ELECTROCAUTERY PEN TIP COVER

(71) Applicant: Suzanne Lee Lowry, Atlanta, GA (US)

(72) Inventor: Suzanne Lee Lowry, Atlanta, GA (US)

( * ) Notice: Subject to any disclaimer, the term of this patent is extended or adjusted under 35 U.S.C. 154(b) by 74 days.

(21) Appl. No.: 13/905,069

(22) Filed: May 29, 2013

(65) Prior Publication Data

US 2013/0325005 A1  Dec. 5, 2013

Related U.S. Application Data

(60) Provisional application No. 61/689,108, filed on May 30, 2012.

(51) Int. Cl.
  *A61B 18/14* (2006.01)
(52) U.S. Cl.
  CPC ....... *A61B 18/1477* (2013.01); *A61B 18/1402* (2013.01); *A61B 2018/1475* (2013.01)
(58) Field of Classification Search
  CPC .. A61B 18/1402; A61B 18/04; A61B 18/08; A61B 18/082; A61B 18/12; A61B 18/14; A61B 18/143; A61B 18/1442; A61B 18/1445; A61B 18/1448; A61B 18/1491; A61B 5/150717; A61B 17/3211; A61B 17/0218; A61B 2017/32113; A61B 2017/0046; A61B 2017/00862

USPC .............. 606/45–41; 604/192–198
See application file for complete search history.

(56) References Cited

U.S. PATENT DOCUMENTS

| | | | |
|---|---|---|---|
| 5,035,695 A * | 7/1991 | Weber et al. | 606/42 |
| 5,120,309 A * | 6/1992 | Watts | A61M 5/3271 604/110 |
| 6,022,364 A * | 2/2000 | Flumene et al. | 606/166 |
| 6,616,630 B1 * | 9/2003 | Woehr et al. | 604/110 |
| 7,749,221 B2 * | 7/2010 | Rontal | 606/41 |
| 8,337,468 B1 * | 12/2012 | Reis et al. | 604/198 |
| 2003/0229314 A1 * | 12/2003 | McWethy | A61M 5/326 604/197 |

* cited by examiner

*Primary Examiner* — Michael Peffley
*Assistant Examiner* — Khadijeh Vahdat
(74) *Attorney, Agent, or Firm* — Innovation Capital Law Group, LLP; Vic Lin

(57) ABSTRACT

A cautery pen cover can cover a cautery pen, with little modification thereto, such that the cover must be retracted to both expose the tip and the trigger of the cautery pen. The cover is designed as a protective sleeve that prevents actuation of the cautery pen trigger until the cover is retracted. The cover automatically returns to the covered position when it is released. The cover is always on the cautery pen, whether in use or just lying on the operating field, thereby not requiring users to place and secure the cautery pen in a plastic holster. The cautery pen use various energy sources, such as electro or radio frequency, or any other source that results in cautery or cutting of tissue.

5 Claims, 4 Drawing Sheets

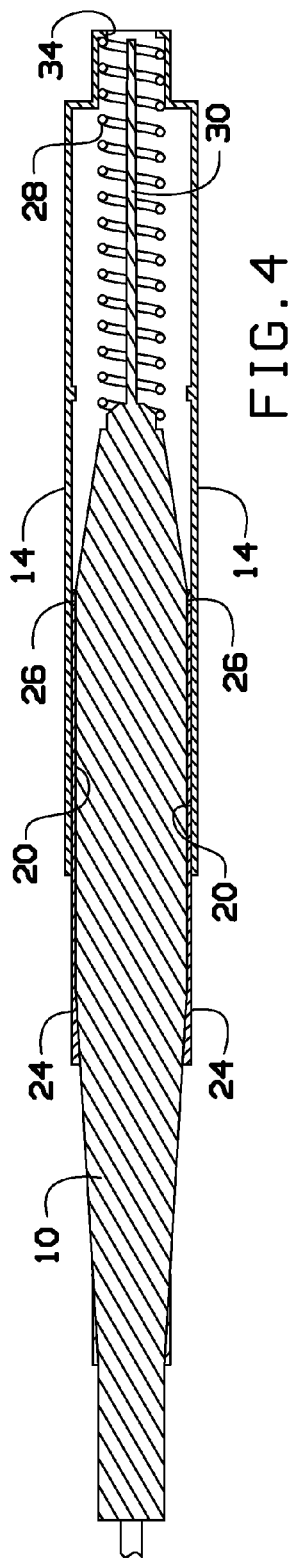
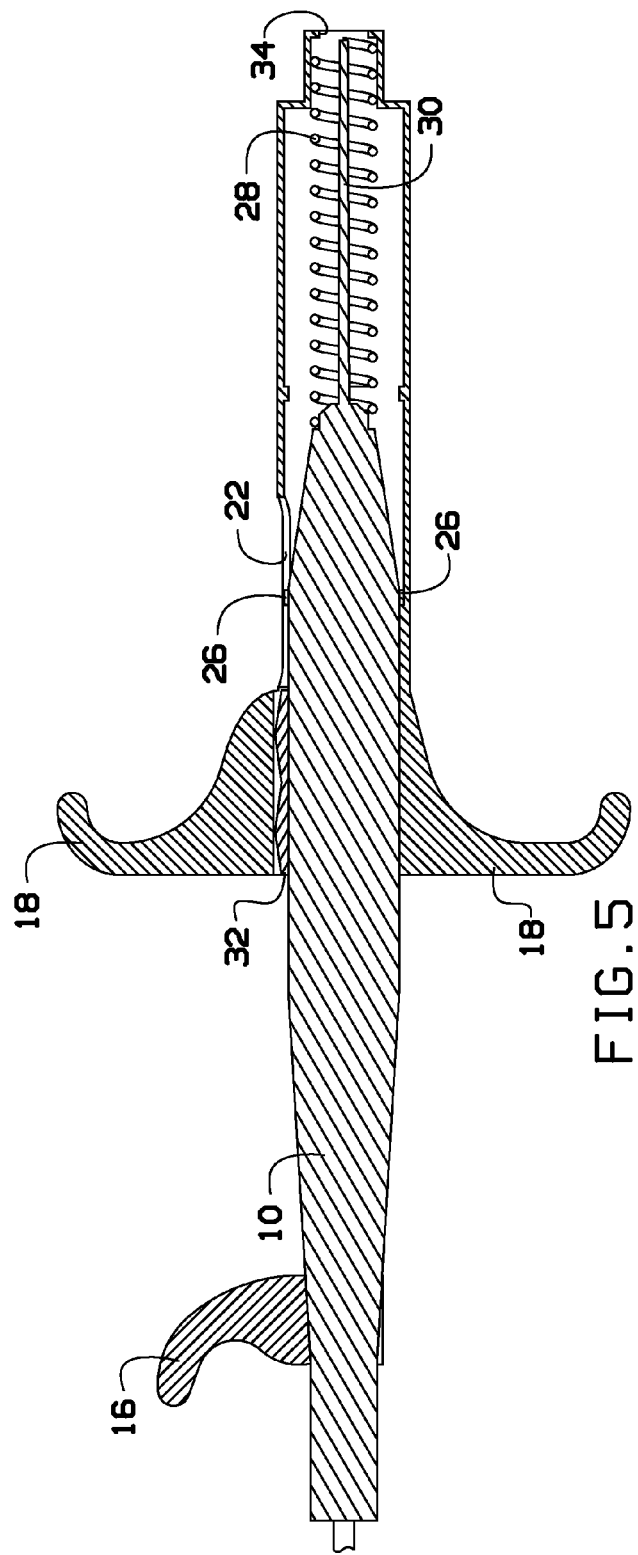

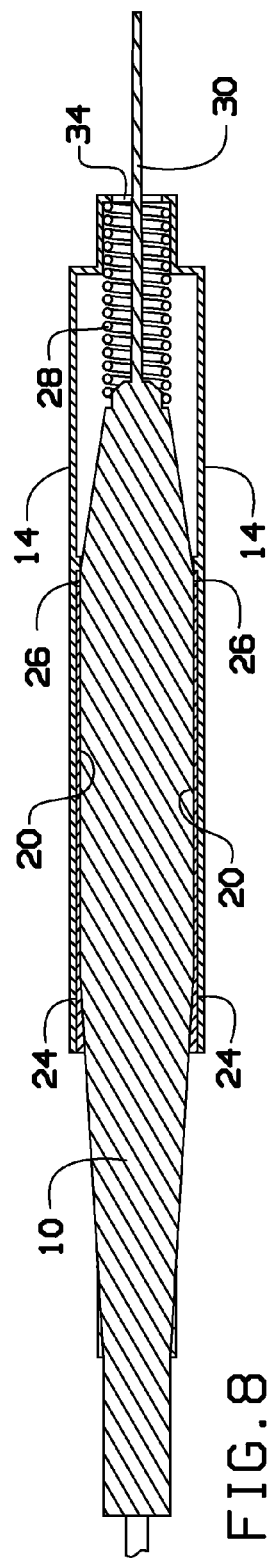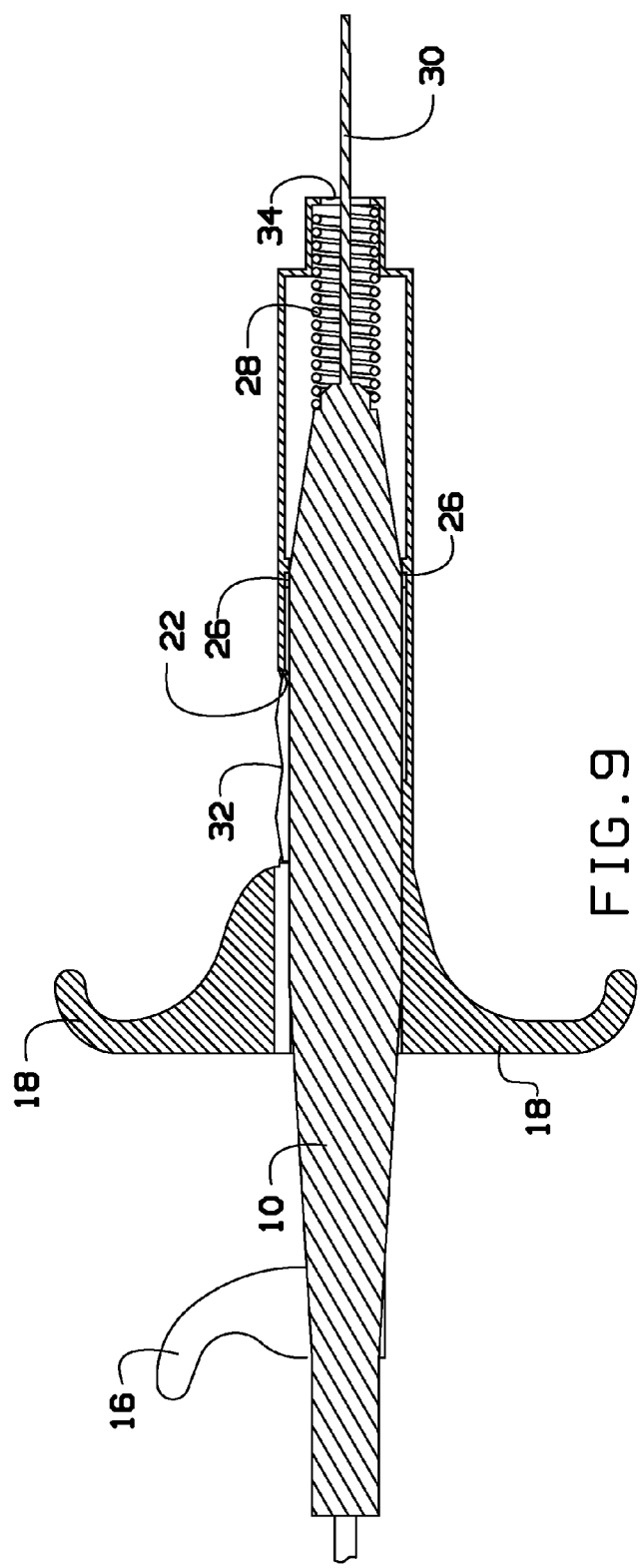
FIG. 8
FIG. 9

COMPRESSION SPRING AUTOMATED RETRACTABLE PROTECTIVE ELECTROCAUTERY PEN TIP COVER

CROSS-REFERENCE TO RELATED APPLICATION

This application claims the benefit of priority of U.S. provisional application Ser. No. 61/689,108, filed May 30, 2012, the contents of which are herein incorporated by reference.

BACKGROUND OF THE INVENTION

The present invention relates to electrocautery accessories and, more particularly, to a compression spring automated retractable protective electrocautery pen tip cover.

Many cautery devices alert the physician and staff through a high-pitched sound. However, this sound is often not heard secondary to all of the many devices in the operating room which make high pitched sounds.

Currently, the only option to assure that the pen is not accidentally actuated by either the surgeon, the staff or even the patient, is to place the pen in a large, clumsy plastic box that is clipped to the operating field. This box is so large that nothing assures that the pen stays in place, other than staff vigilance.

If the pen is dislodged, it can accidently be actuated and start a fire with the oxygen in the room (for anesthesia) or burn the patient before someone realizes it is no longer in the holster. Moreover, the holster often comes off of the tether and the opened tip of the pen is exposed on the operating field. Just leaning on the drapes, for example, can then actuate the opened trigger.

As can be seen, there is a need for a protective cautery pen tip cover that protects the pen tip and prevents accidental actuation of the pen trigger.

SUMMARY OF THE INVENTION

In one aspect of the present invention, a cautery pen tip cover comprises a cylindrical member operable to receive a cautery pen in a first end thereof; a tip opening disposed in a second, opposite end of the cylindrical member, the tip opening permitting a tip of the cautery pen to extend therethrough when the cautery pen tip cover is in a retracted configuration; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; and a resilient member operable to urge the cautery pen tip cover to the non-retracted configuration.

In another aspect of the present invention, a cautery pen tip cover comprises a cylindrical member operable to receive a cautery pen in a first end thereof; a tip opening disposed in a second, opposite end of the cylindrical member, the tip opening permitting a tip of the cautery pen to extend therethrough when the cautery pen tip cover is in a retracted configuration; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; a compression spring operable to urge the cautery pen tip cover to the non-retracted configuration; one or more cover notch guides formed on an inside surface of the cylindrical member, the one or more cover notch guides operable to receive one or more stabilizer tracks disposed on the cautery pen; and at least one cover finger plate extending from the cylindrical member at the first end thereof.

In a further aspect of the present invention, a cautery system comprises a cautery pen; and a cautery pen tip cover, the cautery pen tip cover comprises a cylindrical member operable to receive the cautery pen in a first end thereof; a tip opening disposed in a second, opposite end of the cylindrical member, the tip opening permitting a tip of the cautery pen to extend therethrough when the cautery pen tip cover is in a retracted configuration; a cover exposure opening formed in the cylindrical member, the cover exposure opening providing access to a trigger of the cautery pen when the cautery pen tip cover is in the retracted configuration, wherein the cautery pen tip cover prevents access to the trigger when the cautery pen tip cover is in a non-retracted configuration; and a resilient member operable to urge the cautery pen tip cover to the non-retracted configuration.

These and other features, aspects and advantages of the present invention will become better understood with reference to the following drawings, description and claims.

BRIEF DESCRIPTION OF THE DRAWINGS

FIG. 4 is a cross-sectional view taken along line 4-4 of FIG. 1;

FIG. 5 is a cross-sectional view taken along line 5-5 of FIG. 1;

FIG. 8 is a cross-sectional view taken along line 8-8 of FIG. 6; and

FIG. 9 is a cross-sectional view taken along line 9-9 of FIG. 6.

DETAILED DESCRIPTION OF THE INVENTION

Figure 1:
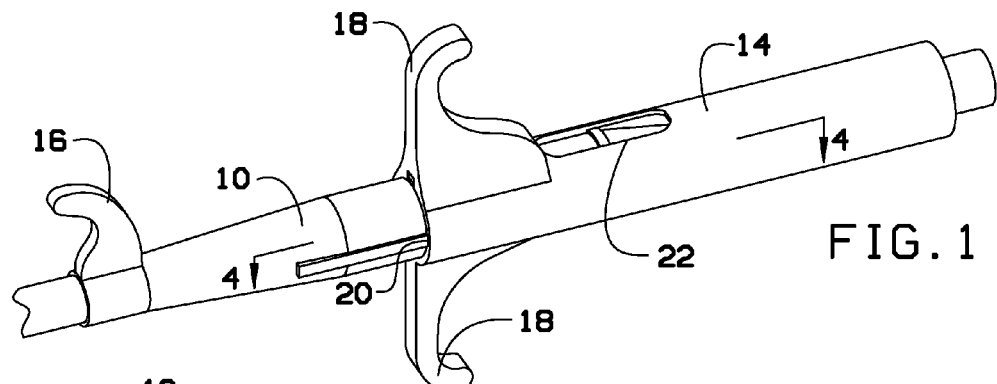
FIG. 1 is a rear perspective view of a cautery pen tip cover, in use on a cautery pen, in a non-retracted configuration, according to an exemplary embodiment of the present invention.
Figure 2:
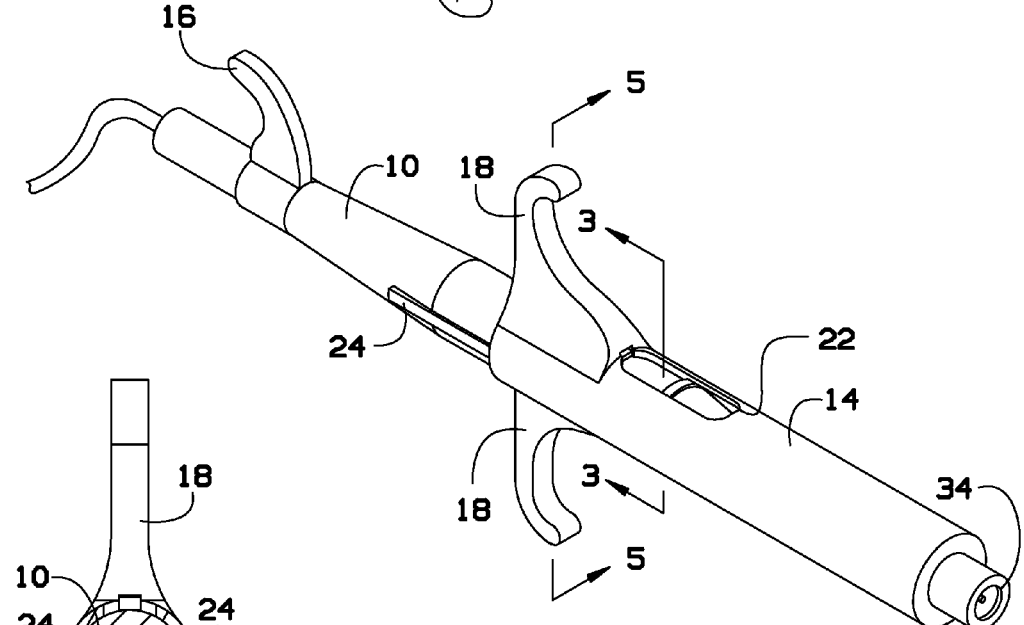
FIG. 2 is a rear perspective view of the cautery pin tip cover of FIG. 1 in use on a cautery pen.
Figure 3:
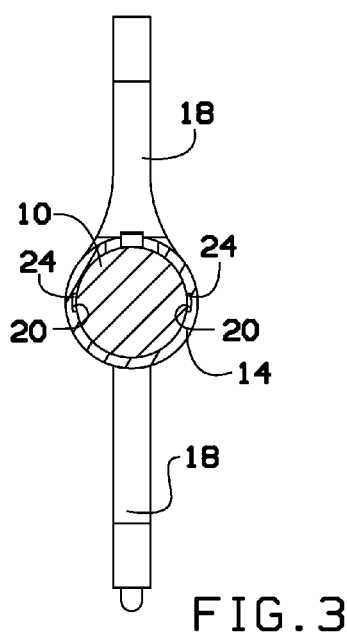
FIG. 3 is a cross-sectional view taken along line 3-3 of FIG. 2.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a cautery pen cover that can cover a cautery pen, with little modification thereto, such that the cover must be retracted to both expose the tip and the trigger of the cautery pen. The cover is designed as a protective sleeve that prevents actuation of the cautery pen trigger until the cover is retracted. The cover automatically returns to the covered position when it is released. The cover is always on the cautery pen, whether in use or just lying on the operating field, thereby not requiring users to place and secure the cautery pen in a plastic holster. The cautery pen use various energy sources, such as electro or radio frequency, or any other source that results in cautery or cutting of tissue.

Referring to FIGS. 1 through 9, an electrosurgical device 10 includes a tip 30 and a trigger 32 for energizing the tip for its intended operation, such as cauterization. The electrosurgical device 10 can further include one or more stabilizer tracks 24 disposed lengthwise along at least a portion of the electrosurgical device 10. A capture ring 26 can be disposed about the electrosurgical device 10, proximate to the tip 30. A resistance bar 16 can extend from the electrosurgical device 10, distal the tip 30, proximate its power cord. In some embodiments, the stabilizer tracks 24, the capture ring 26 and the resistance bar 16 can be provided in a kit with the cover 14 (described below) to convert a conventional electrosurgical device to one that can utilize the cover of the present invention. In other embodiments, the stabilizer tracks 24, the capture ring 26 and the resistance bar 16 can be integrated into the electrosurgical device so that the cover 14 of the present invention can be used therewith. In either case, the additions of the stabilizer tracks 24, the capture ring 26 and the resistance bar 16 to the electrosurgical device does not change the function of the device, with or without use of the cover 14 of the present invention.

The cover 14 can be a cylindrical member having one or more cover notch guides 20 cut into an interior wall of the cylindrical member. The cover notch guides 20 are operable to receive the stabilizer tracks 24 disposed on the electrosurgical device 10. The stabilizer tracks 24, fitting into the cover notch guides 20, prevents rotation of the cover 14 about the electrosurgical device 10.

Figure 6:
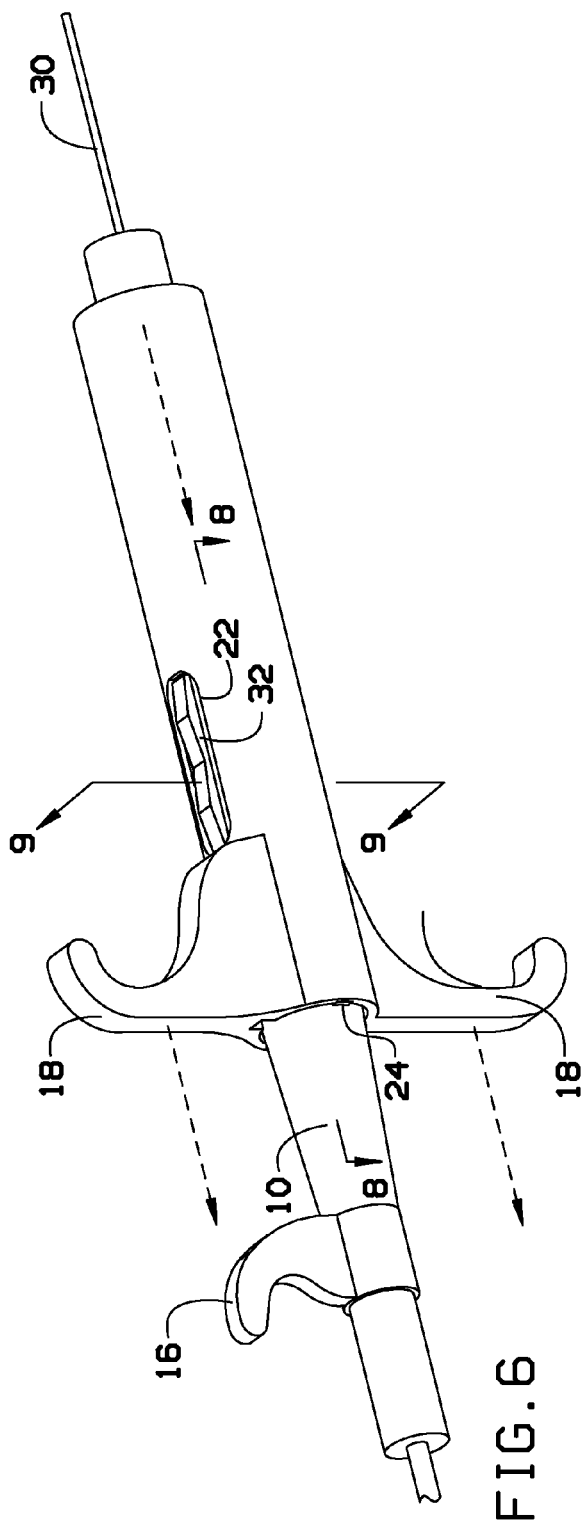
FIG. 6 is a rear perspective view of the cautery pen tip cover of FIG. 1, in use on a cautery pen, in a retracted configuration.
Figure 7:
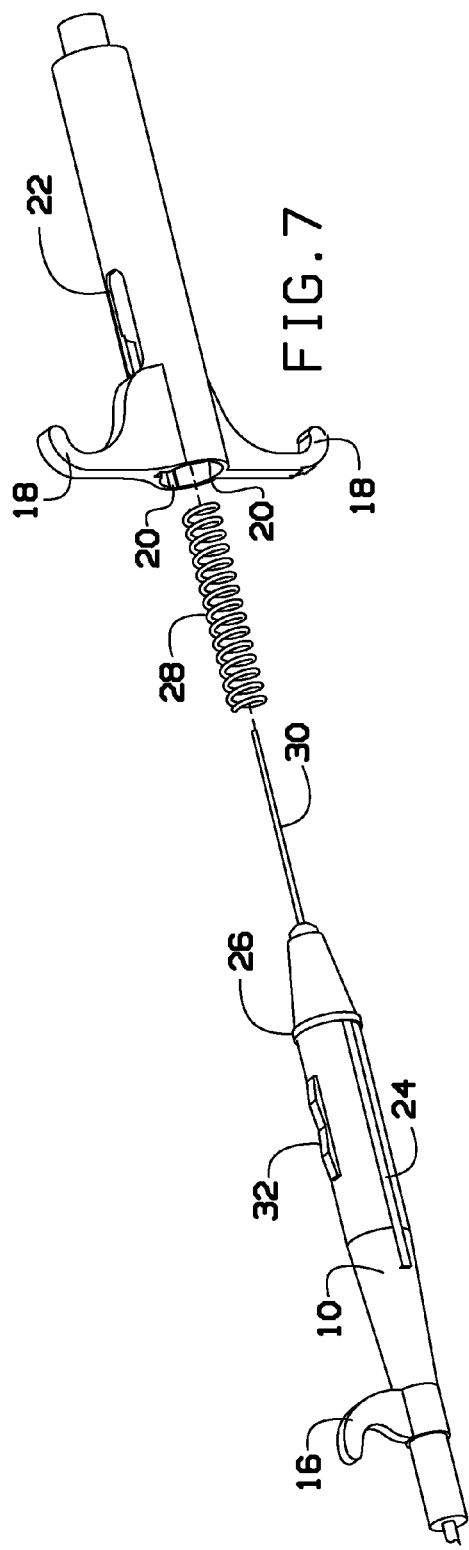
FIG. 7 is an exploded view of the cautery pen tip cover and cautery pen of FIG. 1.

A cover exposure opening 22 can be provided in the cover 14 such that, when the cover 14 is pulled into a retracted configuration (as shown in FIG. 6, for example) where the tip 30 extends from a tip opening 34 of the cover 14, the trigger 32 is accessible through the cover exposure opening 22. Thus, the trigger 32 can only be accessed with the cover 14 is moved into the retracted configuration.

One or more cover finger plates 18, typically two cover finger plates 18, can extend from the cover 14 to provide a mechanism for retracting the cover 14 to expose the tip 30 and permit access to the trigger 32 through the cover exposure opening 22.

A resilient member, such as a compression spring 28, can be disposed inside the cylindrical member of the cover 14 such that, when in the retracted configuration, the resilient member applies a force to urge the cover 14 to a non-retracted configuration, where the tip 30 is inside the cover 14 and the trigger 32 is no longer accessible. The compression spring 28 can be, for example, a ½ inch by 1.5 inch by 0.041 inch compression spring with a working load of 6.84 pounds. With the compression spring 28 keeping the electrosurgical device 10 in a non-retracted position, the device 10 can be laid anywhere in the operative field and remain safe from accidental actuation.

The cover 14 and related components can be made from various materials known in the art. For example, the cover 14 can be made from a molded plastic.

The cover 14 can be used on any and all forms of cautery, whether electrocautery, radio frequency or J plasma. The user could become accustomed to retracting the cover to expose the trigger and the tip simultaneously, removing the option of carelessness while increasing safety.

The design of the present invention can be extended to other devices, such as all sharps and tips of any manner that might cause harm by impaling or cutting.

It should be understood, of course, that the foregoing relates to exemplary embodiments of the invention and that modifications may be made without departing from the spirit and scope of the invention as set forth in the following claims.

What is claimed is:

1. A cautery system comprising:
   a cautery pen; and
   a cautery pen tip cover, the cautery pen tip cover comprising:
      a cylindrical member operable to removeably receive the cautery pen in a first open end thereof, the cautery pen having a trigger on its housing, the trigger actuating the cautery pen, where the cautery pen is operable outside of the cylindrical member by actuation of the trigger;
      a tip opening disposed in a second, opposite end of the cylindrical member, the tip opening permitting a tip of the cautery pen to extend therethrough when the cautery pen tip cover is in a retracted configuration;
      a cover exposure opening formed in the cylindrical member, the cover exposure opening formed as a through hole in the cylindrical member allowing a user to directly contact the trigger of the cautery pen only when the cautery pen tip cover is in the retracted configuration, wherein the cautery pen tip cover prevents access to the trigger when the cautery pen tip cover is in a non-retracted configuration; and
      a resilient member operable to urge the cautery pen tip cover to the non-retracted configuration.

2. The cautery system of claim 1, further comprising one or more cover notch guides formed on an inside surface of the cylindrical member, the one or more cover notch guides operable to receive one or more stabilizer tracks disposed on the cautery pen.

3. The cautery system of claim 1, further comprising at least one cover finger plate extending from the cylindrical member at the first end thereof.

4. The cautery system of claim 1, wherein the resilient member is a compression spring.

5. The cautery system of claim 1, further comprising a resistance bar extending from the cautery pen, distal the tip of the cautery pen.

* * * * *